United States Patent [19]

Horton

[11] Plant 4,651

[45] Feb. 17, 1981

[54] ALMOND TREE

[75] Inventor: Cecil V. Horton, 14923 W. Westside Blvd., Livingston, Calif. 95334

[73] Assignees: Cecil V. Horton; Dorothy Horton, both of Livingston, Calif.

[21] Appl. No.: 104,880

[22] Filed: Dec. 18, 1979

[51] Int. Cl.[3] ..... A01H 5/03

[52] U.S. Cl. ..... Plt./30

[58] Field of Search ..... Plt./30

*Primary Examiner*—Robert E. Bagwill

*Attorney, Agent, or Firm*—Roger B. Webster

[57] ABSTRACT

An almond tree which is dense, medium size, vigorous, stocky of trunk and branches, both with medium texture, spreading, abundantly foliated with large, lanceolate, acutely pointed leaves having a finely serrate margin and green, globose, opposite-alternate glands, blooms heavily with pink flowers, and is a regular and very heavy bearer of small, ovate, well-sealed, well-distributed nuts.

1 Drawing Figure

BACKGROUND OF THE VARIETY

FIELD OF THE DISCOVERY

The present new and distinct variety of almond tree is embraced by subclass 30, Plants, of the United States Patent Office Manual of Classification.

PRIOR VARIETIES

Among the existent varieties of almond tree which are known to me, and mentioned herein, are Nonpareil and Mission (both unpatented).

ORIGIN OF THE VARIETY

The present variety of almond tree—while its origin is unknown—was discovered by me growing on my premises located near Livingston, Merced County, Calif.; the tree having been initially permitted to grow for shade. However, in its maturity, I recognized that the tree had certain new and distinctive characteristics—as will hereinafter appear—and I, therefore, determined to effect asexual reproduction of the tree, with a view toward ultimate commercialization of the variety.

ASEXUAL REPRODUCTION OF THE VARIETY

The present variety of almond tree was asexually reproduced, on my behalf and by a commercial nursery, by June budding, and such asexual reproductions—in maturity—ran true to the original tree in all respects.

SUMMARY OF THE VARIETY

The present variety of almond tree is dense, medium size, vigorous, stocky of trunk and branches, both with medium texture, spreading, abundantly foliated with large, lanceolate, acutely pointed leaves having a finely serrate margin and green, globose, opposite-alternate glands, blooms heavily with pink flowers, and is a regular and very heavy bearer of small, ovate well-sealed, well-distributed nuts.

The present variety of almond tree is further characterized, in comparison to the Mission, by:

A tree which is more spreading, and in this respect distinct from the more erect Mission.

In bloom several days earlier than the Mission, and interfertile with the Nonpareil.

Well-sealed nuts which are similar in size and shape, but with larger shell pits and a softer, duller corky surface.

Kernels which are slightly longer and milder in flavor.

The present variety of almond tree is still further characterized, in comparison to the Nonpareil, by a harvest period which is approximately three weeks later.

BRIEF DESCRIPTION OF THE DRAWING

The drawing is an illustration, by photographic reproduction in color, of a twig with leaves and nuts in hull, and, separately, a nut in half hull, nuts out of hull, and kernels out of shell.

DESCRIPTION OF THE VARIETY

The botanical details of this new and distinct variety of almond tree—with color definitions (except those in common color terms) referenced to Maerz and Paul Dictionary of Color—are as follows:

Tree:
- *Density.*—Dense.
- *Size.*—Medium.
- *Vigor.*—Vigorous.

Trunk:
- *Form.*—Stocky.
- *Texture.*—Medium.

Branches:
- *Form.*—Stocky.
- *Texture.*—Medium.
- *Lenticels.*—Number—numerous. size—medium. Branching habit—spreading. Color—New wood—red—brown. Dull. Mature wood—gray. Dull.

Foliage:
- *Quantity.*—Abundant.

Leaves:
- *Size.*—Large. Average length—4½". Average width—1¼".
- *Shape.*—Lanceolate. Acutely pointed.
- *Thickness.*—Medium.
- *Texture.*—Smooth.
- *Margin.*—Finely serrate.
- *Petiole.*—Medium length.

*Glands.*—Average number—2. Opposite—alternate (more opposite than alternate). Small. Globose. Green. Positioned on petiole adjacent leaf blade.

*Stipules.*—None.

*Color.*—Top side—Medium glossy green (22-J-8). Under side—Lighter dull green (22-L-7).

Bloom:

*Amount of bloom.*—Heavy.

*Color of bloom.*—Pink.

*Blooming period.*—Approximately with Nonpareil.

Crop:

*Bearing.*—Regular bearer.

*Productivity.*—Very heavy.

*Distribution of nuts on tree.*—Well distributed.

*Harvest period.*—Approximately three weeks after Nonpareil.

*Tenacity.*—Hangs well on tree. Easy to hull.

Hull:

*Outer surface.*—Smooth.

*Pits.*—Unpitted.

*Form.*—Regular.

*Thickness.*—Thick.

*Flesh.*—Fleshy.

*Suture.*—Smooth.

*Color.*—Light uniform green (21-K-7) without a silvery sheen.

*Dehiscence.*—Opens partially.

*Splitting.*—Along suture. Freely at base.

Nut:

*Size.*—Small. Average length—1⅛". Average width—11/16". Average thickness—9/16". Average weight—14 per ounce.

*Form.*—Length/width—ovate. Width/thickness—plump.

*Shell.*—Soft. Thick. Smooth. Outer shell—crumbling. Inner shell—hard. Well sealed.

*Color.*—Medium light brown (13-L-7).

*Pits.*—Large. Numerous. Deep. Round.

*Base.*—Square.

*Stem scar.*—Large. Obtuse.

*Apex.*—Acute. Acuminate.

*Wing.*—Narrow. Thin. Tapered toward base.

*Inner surface.*—Dark colored.

*Ventral streak.*—Narrow. Long. Point acute.

*Percentage of kernel to nut.*—48.6%.

Kernel:

*Size.*—Small. Average length—13/16". Average width—½". Average thickness—½". Average weight—26 per ounce.

*Form.*—Length/width—wedge. Width/thickness—plump.

*Base.*—Ventrally oblique.

*Stem scar.*—Large. Obtuse.

*Apex.*—Acute. Acuminate.

*Texture.*—Furrowed.

*Pellicle.*—Thin.

*Pubescence.*—Smooth. Veined.

*Color.*—Medium brown (14-H-11).

*Number of doubles.*—Few.

*Defective kernels.*—None observed.

*Flavor.*—Sweet.

*Quality.*—Good.

Resistance to insects and diseases: Comparable to Nonpareil.

Summarizing: The present variety of almond tree is—by virtue of heavy blooming several days earlier than the Mission and interfertility with the Nonpareil—especially adapted for inter-planting with the latter; and this characteristic, together with tree vigor, regular and heavy production of well-sealed nuts and a harvest period approximately three weeks after the Nonpareil, evidences the value of the present variety for commercial production. The blooming of the present variety several days earlier than the Mission assures and provides pollen for the first Nonpareil blossoms, and as a consequence the present variety and the Nonpareil are an excellent orchard combination.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, characterized by a vigorous tree having regular and heavy production of well-sealed nuts; and further characterized by blooming several days earlier than the Mission and interfertile with the Nonpareil, and by a harvest period approximately three weeks after the latter.

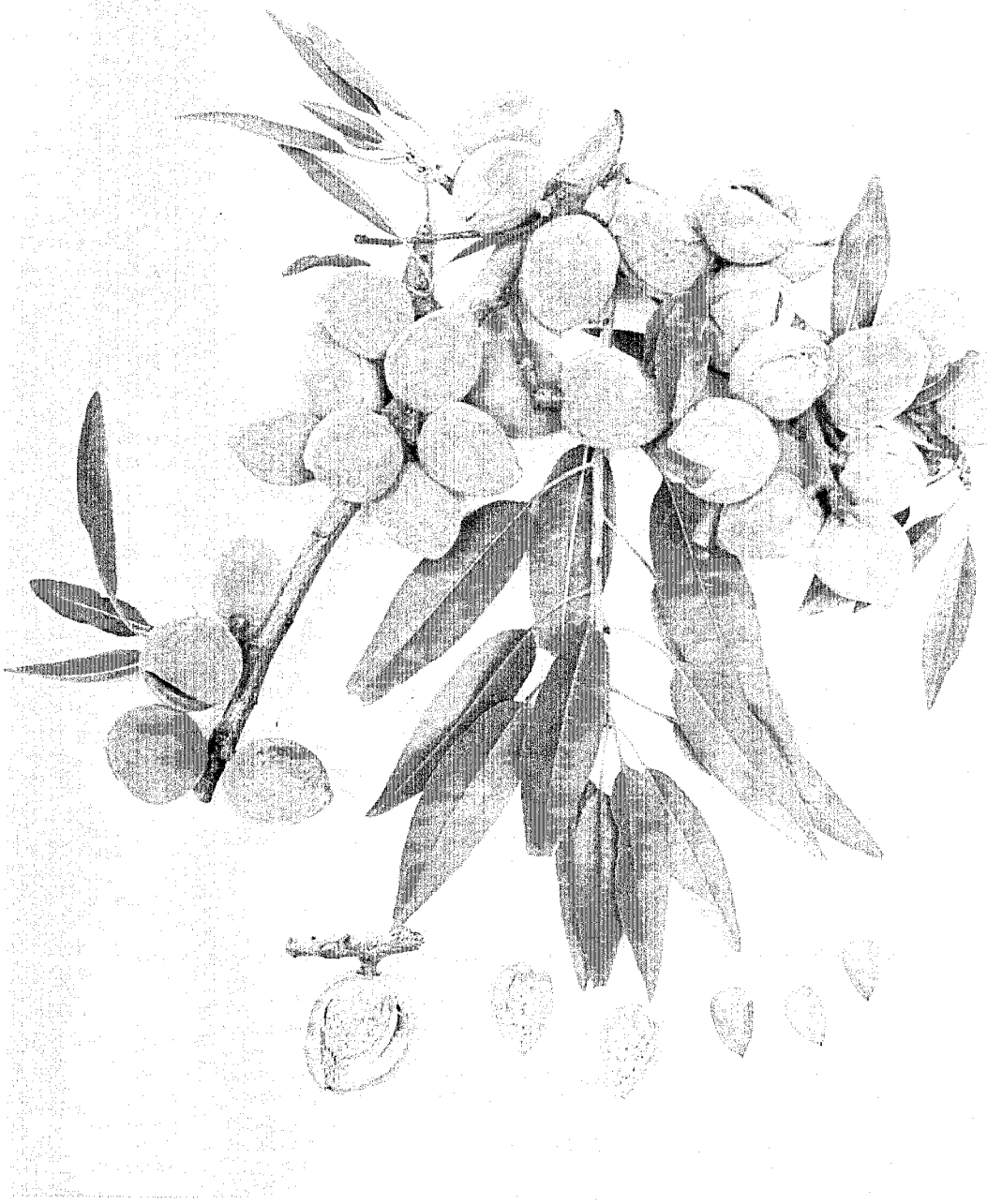

* * * * *